(12) United States Patent
Kimonides

(10) Patent No.: US 8,061,221 B2
(45) Date of Patent: Nov. 22, 2011

(54) LIQUID SAMPLING APPARATUS

(75) Inventor: Riginos Kimonides, Stamford (GB)

(73) Assignee: UK Sampling Gauges Limited, Essendine, Stamford (GB)

( * ) Notice: Subject to any disclaimer, the term of this patent is extended or adjusted under 35 U.S.C. 154(b) by 395 days.

(21) Appl. No.: 11/996,508

(22) PCT Filed: May 22, 2006

(86) PCT No.: PCT/GB2006/001868
§ 371 (c)(1),
(2), (4) Date: Jan. 23, 2008

(87) PCT Pub. No.: WO2006/125966
PCT Pub. Date: Nov. 30, 2006

(65) Prior Publication Data
US 2008/0196516 A1 Aug. 21, 2008

(30) Foreign Application Priority Data

May 23, 2005 (GB) .................................. 0510477.3
Apr. 10, 2006 (GB) .................................. 0607092.4

(51) Int. Cl.
*G01N 1/12* (2006.01)
(52) U.S. Cl. ........................................ 73/864.63
(58) Field of Classification Search ............... 73/864.63
See application file for complete search history.

(56) References Cited

U.S. PATENT DOCUMENTS

| | | | |
|---|---|---|---|
| 540,121 A | 5/1895 | Tagliabue | |
| 1,621,857 A | 3/1927 | Seraphin | |
| 2,071,145 A | 2/1937 | Summers | |
| 2,155,601 A | 4/1939 | Johnson | |
| 2,166,779 A | 7/1939 | Arntzen | |
| 2,192,065 A | 2/1940 | Sandstone | |
| 2,607,229 A | 8/1952 | Quist | |
| 2,713,269 A | 7/1955 | Neer | |
| 3,625,065 A * | 12/1971 | Thompson | ............... 73/863.51 |
| 3,680,389 A | 8/1972 | Binkley, Jr. et al. | |
| 4,004,463 A | 1/1977 | Puthoff et al. | |
| 4,590,810 A | 5/1986 | Hunkin et al. | |
| 4,790,197 A | 12/1988 | Kimonides | |
| 4,928,541 A | 5/1990 | Toon et al. | |

FOREIGN PATENT DOCUMENTS

| | | |
|---|---|---|
| DE | 352600 | 5/1922 |
| DE | 489490 C | 1/1930 |
| DE | 9207725 U1 | 12/1992 |
| DE | 10314512 A1 | 10/2004 |

(Continued)

OTHER PUBLICATIONS

Discrete Depth Groundwater Sampler, Sample Container and Monitor, IBM Technical Disclosure Bulletin, IBM Corp., New York, NY, vol. 33, No. 10B, Mar. 1, 1991, pp. 334-335.

*Primary Examiner* — Hezron E Williams
*Assistant Examiner* — Alex Devito
(74) *Attorney, Agent, or Firm* — Richard M. Goldberg

(57) ABSTRACT

A sampling apparatus for taking a liquid sample includes an inlet, a sample housing defining a sampling chamber for the liquid sample, and a sampling tube through which, in use, a flow of liquid to be sampled flows from the inlet into the sampling chamber. The sampling tube extends a predetermined distance within the sampling chamber, and defines a fluid pathway between the inlet and the sampling chamber.

15 Claims, 6 Drawing Sheets

FOREIGN PATENT DOCUMENTS

| | | |
|---|---|---|
| EP | 1076233 A3 | 2/2001 |
| GB | 330317 | 6/1930 |
| GB | 566752 | 1/1945 |
| GB | 674166 | 6/1952 |
| GB | 903378 | 8/1962 |
| GB | 958916 | 5/1964 |
| GB | 1107180 | 3/1968 |
| GB | 2032885 A | 5/1980 |
| GB | 2040265 A | 8/1980 |
| GB | 2072145 A | 9/1981 |
| GB | 2170477 A | 8/1986 |
| GB | 2203406 A | 10/1988 |
| GB | 2236522 A | 4/1991 |
| WO | 03098191 A3 | 11/2003 |

* cited by examiner

LIQUID SAMPLING APPARATUS

BACKGROUND OF THE INVENTION

This invention relates to an apparatus for liquid sampling. In particular, it relates to an apparatus for obtaining a liquid sample from a body of liquid along a depth range, which is representative of the liquid along the entire depth range.

When a liquid, for example oil, is stored in large volumes, the properties and composition of the liquid can vary significantly at different depths. A sample removed from a single point within such a body of liquid will only provide information on the composition at that specific depth within the liquid, and does not provide an accurate representation of the entire body of liquid. Therefore, to obtain accurate readings relating to, and representative of an entire body of liquid, it is necessary to obtain a sample taken along the entire depth of the liquid. Furthermore, it is not sufficient to merely take multiple samples from a number of specified depth points as important variations in the liquid properties along the depth may be ignored. This is particularly important in liquid such as oils in which stratified layers may form.

Accordingly, a number of current sampling systems continuously sample liquid whilst traversing the depth of a body of liquid. Such systems generally comprise a sampling container having multiple sampling apertures located at the top of chamber. As the sampling chamber is lowered through the liquid, the liquid pressure forces liquid into the chamber via one or some of the apertures, while the remaining apertures allow air from within the chamber to escape. However, as the sampling chamber descends within the liquid, the liquid pressure increases, resulting in an increase in flow rate of the liquid into the chamber. Hence, the sampling flow rate is not constant as the container descends along the sampled depth range. As a result, the liquid sample will generally contain a greater volume of liquid from the lower end of the sampling range than from the upper end. Therefore, whilst such systems improve on single depth sampling techniques, they fail to provide samples which are representative of the entire depth range sampled. In addition, as such samplers are raised back through the body of liquid once the sampling has been completed, at least the upper levels of the sample are contaminated as liquid continues to enter the chamber and mix with the sample already taken.

It is therefore desirable to provide an improved system for sampling liquids which addresses the above problems, and provides a sample representative of the entire sample depth range, and/or which provides improvement generally.

SUMMARY OF THE INVENTION

According to the present invention there is provided a liquid sampling apparatus, as described in the accompanying claims.

In a first aspect of an embodiment of the invention there is provided a sampling apparatus for taking a liquid sample. The apparatus comprises an inlet, a sample housing defining a sampling chamber for the liquid sample, and an inner sampling tube through which in use a flow of liquid to be sampled flows from the inlet into the sampling chamber. The inner sampling tube is located and extends a predetermined distance into and within the sampling chamber.

Preferably the inner sampling tube has an outlet spaced a predetermined distance from the inlet and through which in use the liquid sample flows into the sampling chamber.

In preferred embodiment of the invention, the sampling apparatus is arranged such that the outlet of the inner sampling tube is in use vertically disposed above the inlet. The inner sampling tube in use thereby defines a fixed constant inlet pressure head for fluid flowing into the sampling apparatus.

The inlet preferably further comprises an inlet valve assembly. The inlet valve assembly comprises an inlet aperture and a non-return valve.

The sampling apparatus may further comprise an outlet. Preferably, the outlet comprises an outlet valve assembly. The outlet valve assembly has an outlet aperture and a non-return valve.

The sampling apparatus preferably comprises a base cap and an end cap, connected to opposing ends of the sample housing. The base cap comprises a base cap section and an inlet valve assembly comprising the inlet, and the end cap comprises an end cap section and an outlet valve assembly comprising the outlet. The sampling apparatus is oriented in use such that the end cap is vertically disposed above the base cap. The inlet is therefore in use at a greater liquid pressure than the outlet, thereby forcing liquid to flow into the sampling chamber through the inlet.

The sampling apparatus is preferably arranged such that the flow rate of liquid into the sampling chamber is constant and independent of the external liquid pressure.

In another aspect of an embodiment of the invention, there is provided a sampling apparatus for taking a liquid sample. The apparatus comprises a sample housing defining a sampling chamber for the liquid sample, and an inlet comprising an inlet valve assembly, through which the liquid to be sampled flows into the sampling chamber. The inlet valve assembly comprises an inlet aperture, a body section and a collar. The collar is slidably attached to the body section, and is slidable between a first position and a second position. In the first position the collar covers the inlet aperture, thereby preventing in use the passage of liquid therethrough. In the second position, the inlet aperture is uncovered, such that in use passage of liquid therethrough is enabled. The collar thereby in use only permits liquid to enter the inlet aperture when the sampling apparatus is descending within liquid. When in use the sampling apparatus is stationary or moving upwardly, the collar seals the inlet aperture.

The collar is preferably biased to the first position. The collar may be biased to the first position by its own weight. Alternatively, a resilient means is provided to bias the collar to the first position.

In another aspect of an embodiment of the invention, there is provided a sampling apparatus for taking a liquid sample. The apparatus comprises an inlet, a sample housing defining a sampling chamber for the liquid sample, and an outlet valve assembly. The outlet valve assembly comprises a valve having a sealing member, and a resilient member, the valve being biased to a closed position by the resilient member, and a key member having a pin. The key member is attachable to the valve by a screw thread such that the pin extends towards the sealing member of the valve. The key member may turned within the thread of the valve is use, such that the pin engages the sealing member thereby opening the valve. The key member thereby enables in use the valve to be selectively opened or closed by insertion or removal of the key member therein or therefrom.

BRIEF DESCRIPTION OF THE DRAWINGS

The invention will now be described by way of example only with reference to the accompanying drawings in which.

DETAILED DESCRIPTION

Figure 1:
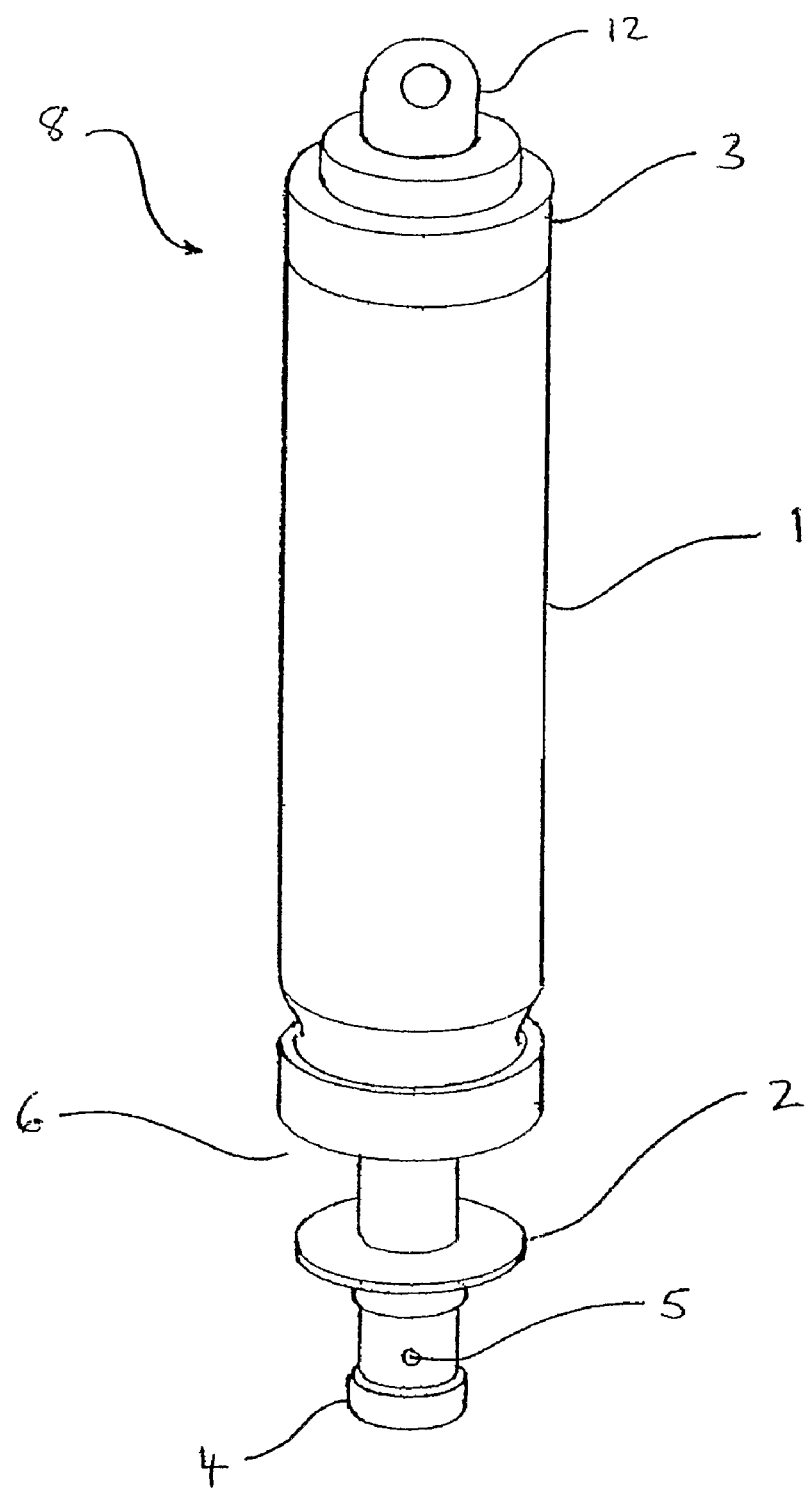
FIG. 1 is a perspective view of the sampling apparatus.
Figure 2:
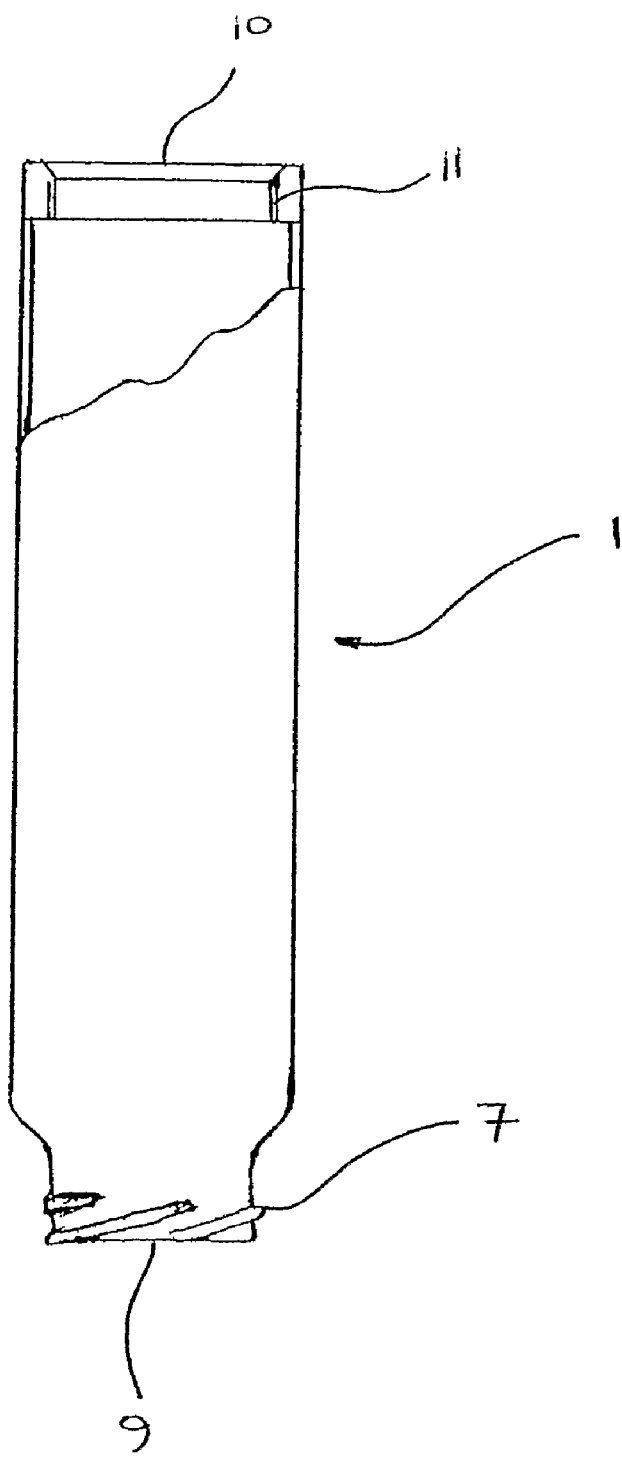
FIG. 2 is a partial section of the sampling chamber.
Figure 3:
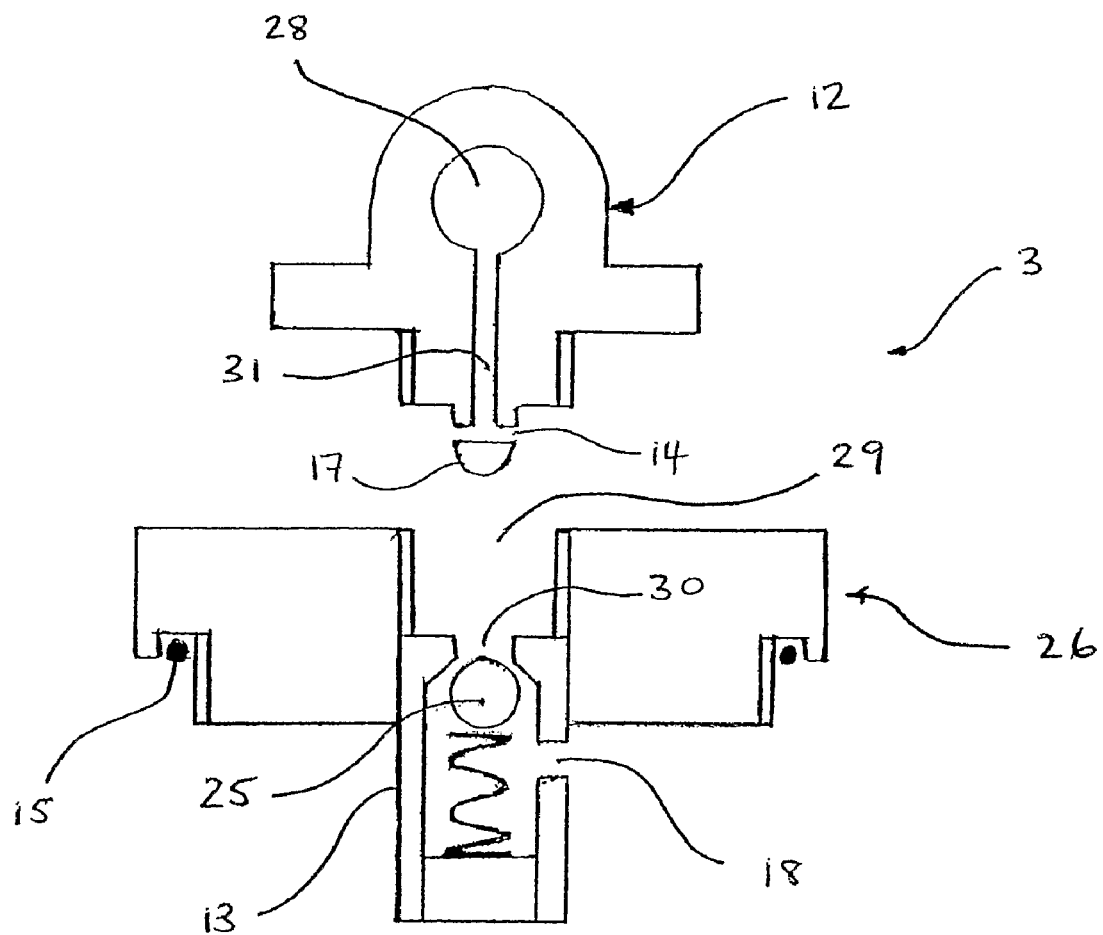
FIG. 3 is a section view of the key valve assembly.
Figure 4:
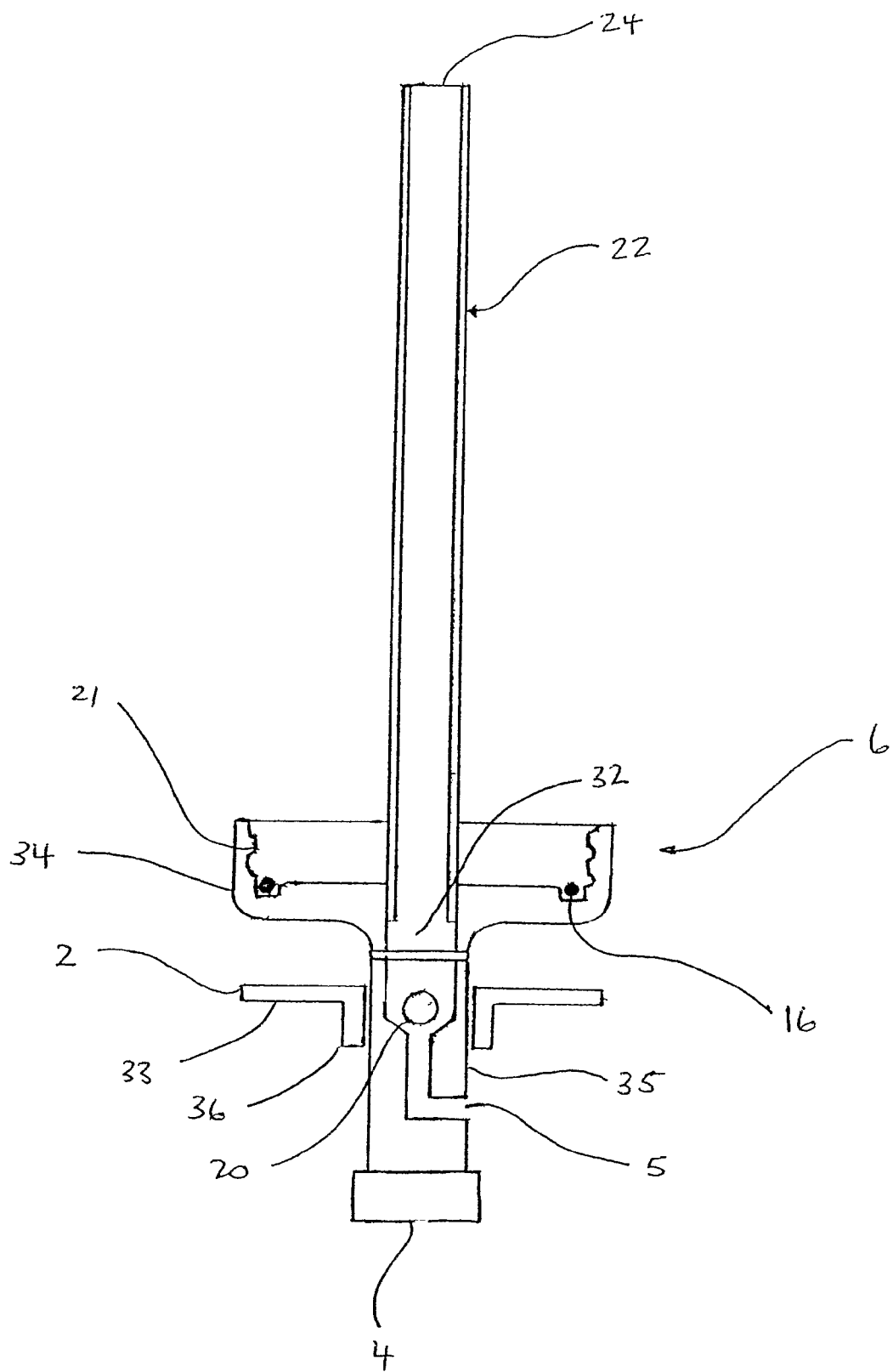
FIG. 4 is a section view of the inlet valve and inner sampling tube.
Figure 5:
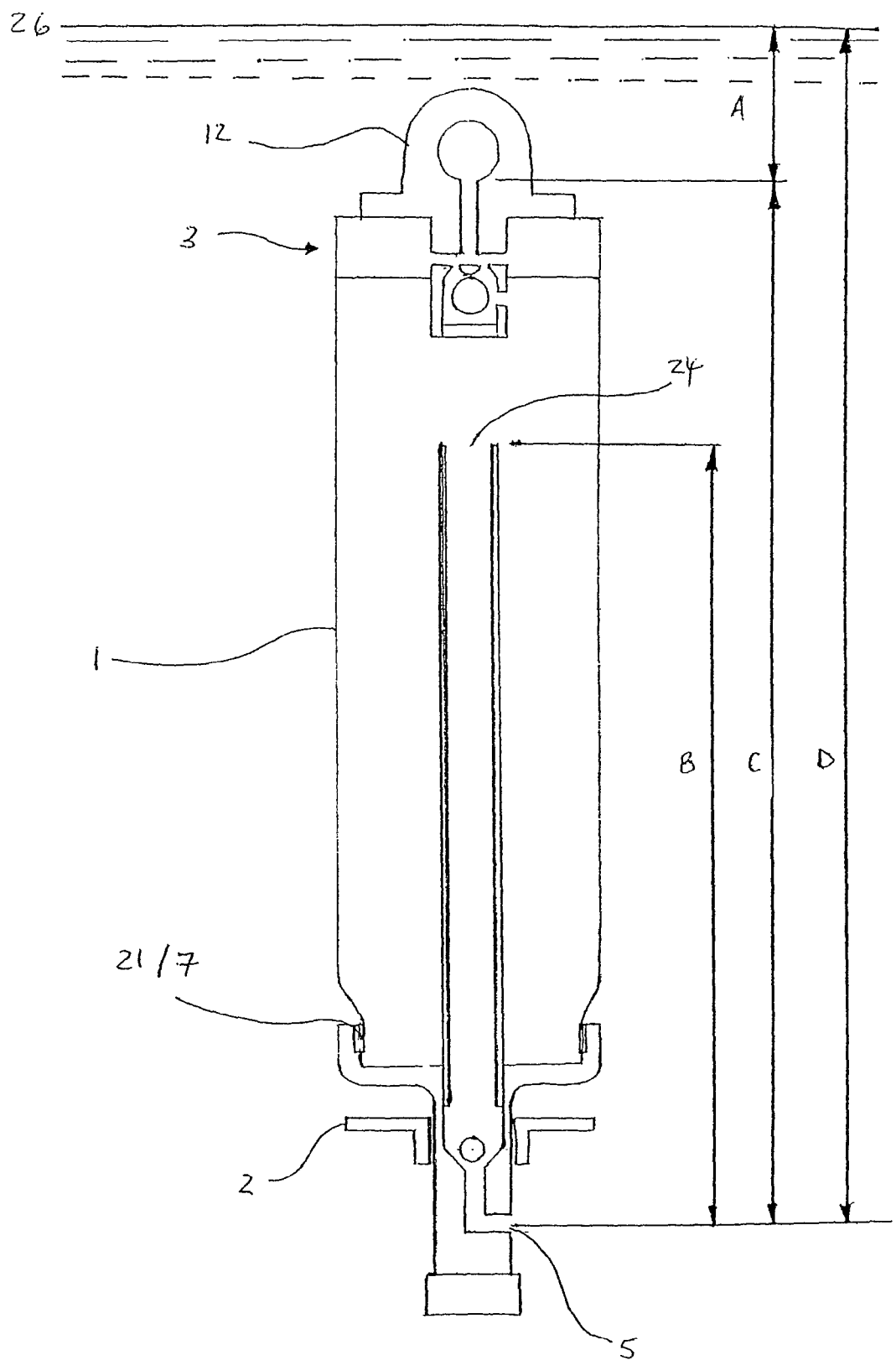
FIG. 5 is a section view of the sampling apparatus.
Figure 6:
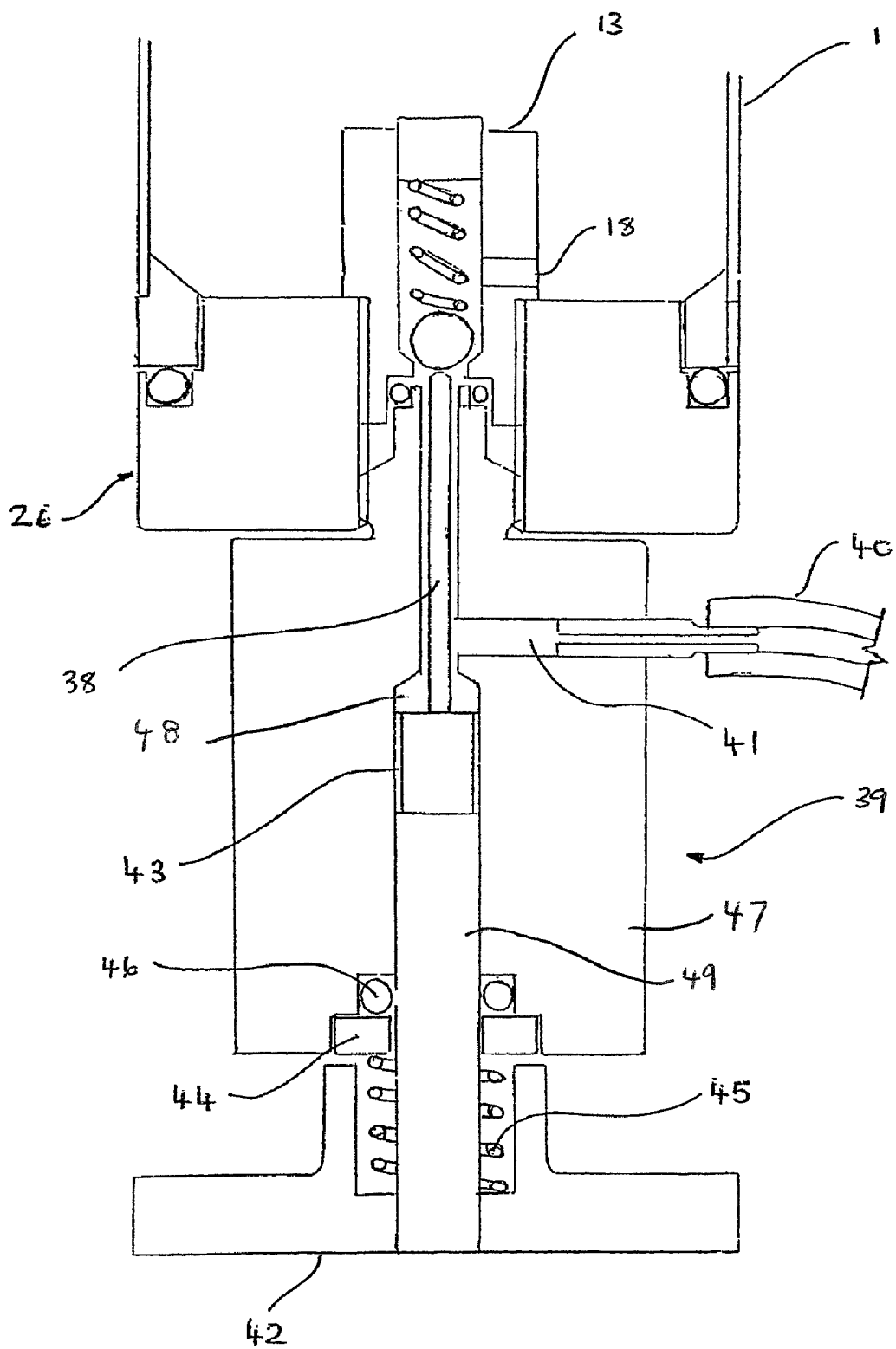
FIG. 6 is a section view of the sampling valve connected to the sampling camber.

Referring to FIG. 1, the sampling apparatus comprises a sample housing 1 defining a sampling chamber, a base cap 6, and an end cap 3. In use, the sampling apparatus 8 is lowered vertically into a body of liquid to obtain a sample thereof. The base cap is located at the base of the sample housing 1 and the end cap 3 is located at the top of the sample housing 1. The main body of the sample housing 1 is preferably cylindrical, although such is not essential. The sample housing 1 is preferably made of stainless steel, although it may be made of any other suitable material.

The sample housing 1 is provided with an aperture 10 at the top of the sample housing 1, and an aperture 9 at the base of the sample housing 1. A threaded section 7 is provided at the base of the sample housing 1 for attachment of the base cap 6. The base of the sample housing 1 is preferably reduced in diameter, such that the outer diameter of the base of the housing is less than the outer diameter of the main body of the housing. The top of the sample housing 1 is also provided with a threaded section 11 for attachment of the end cap 3.

The end cap 3 comprises an outlet valve assembly, and cap section 26. An aperture 29 is formed in cap section 26. The outlet valve assembly comprises key member 12 and valve 13. Valve 13 comprises a resilient member, for example a spring, a sealing member 25, for example a ball, and apertures 30 and 18. Cap section 26 is threaded for attachment to sample housing 1, a resilient sealing member 15 is provided in a radially extended groove within cap member 26, for providing an air tight seal with the sample housing 1. Aperture 29 is threaded to permit attachment thereto of key member 12. A pin member 17 extends from the base of key member 12, and an internal bore 14 is provided within pin member 17, which interconnects with internal bore 31 of key member 12.

When the sampling apparatus is not in use, the key member 12 remains separate from cap section 26, such that non return valve 13 is closed. Prior to the commencement of sampling, the key member 12 is attached to cap section 26. As key member 12 is threaded into aperture 29 the pin member 17 progressively extends further within aperture 29 until it begins to push against sealing member 25 of the non return valve 13. As pin member 17 is forced against sealing member 25, the resilient member of the non return valve 13 is compressed such that the seal between sealing member 25 and aperture 30 is broken. A pathway is thereby provided for air to exit from the sampling chamber via apertures 18 and 30, and then through internal bores 14 and 31 of key member 12. In this way, air is able to escape from the sampling chamber as it fills during liquid sampling. Once sampling is completed, the key member 12 is removed from cap member 26, thereby allowing the non return valve 13 to close. In this way, the sampled liquid contained within the sampling chamber is sealed within the sampling chamber, which is essential for preventing escape of liquid or gases from the chamber once sampling is completed. In addition, key member 12 comprises a lug 28 for attachment of a supporting cable or wire, which is used to lower the sampling apparatus during sampling.

Base cap 6 consists of a cap section 34 and a valve section 35. The cap section 34 attaches to the base of sample housing 1 via a threaded section 21. A resilient sealing member 16 is provided within a radial groove in cap section 34 to provide an air tight seal between cap section 34 and the sample housing 1. An inner bore 32 extends within base cap 6. The inner bore 32 extends from the cap section 34 into the valve section 35 where it is restricted before continuing to the inlet aperture 5. A sealing member 20 is provided within the wider section of the inner bore 32 such that the combination of the restricted bore section and the sealing member 20 form a non-return valve which allows fluid to flow into the sampling chamber, but prevents fluid from exiting the sampling chamber once sampling has stopped. A collar 2 surrounds, and is slidably engageable with, the valve section 35. The collar member 2 comprises a main body 36 and a flange section 33 which radially extends therefrom. Alternatively, the collar may comprise a relatively thick disc member which covers and extends over. The collar member 2 is preferably made of nylon, although it may be made of any other suitable material.

The collar member 2 covers and seals the inlet aperture 5 such that liquids or gases are prevented from entering or leaving said aperture 5. The outer diameter of the valve section 5 is increased at its base, such that the outer diameter of the base of valve section 35 is greater than the inner diameter of the collar member 2, thereby acting as an end cap an preventing the collar member 2 from sliding off the end of the valve section 35. Preferably, the outer diameter of the valve section 35 is increased by providing a retaining nut 4 at the base of the inlet valve 6, although any suitable means for locating the collar section in the closed position could be provided. The collar 2 is slidable from the closed position, to an open position, wherein the aperture 5 is uncovered. The collar 2 is biased towards the closed position. Preferably, the collar 2 is biased towards the closed position by its own weight, or by the force of liquid on the its upper surface. Alternatively, the collar may be biased towards the closed position by a resilient member such as a spring.

An inner sampling tube 22 is inserted into the inner bore 32 of base cap 6 such that the inner sampling tube 22 extends upwardly from the base cap 6. The inner sampling tube is preferable cylindrical, and extends within the sampling chamber from the base cap 6. When the base cap 6 is connected to the sample housing 1, the inner sampling tube 22 extends vertically within the sampling chamber. The inner sampling tube 22 does not extend along the full internal height of the sampling chamber 1, such that when the end cap 3 is connected to the top of the sample housing 1 a gap is defined between the end cap 3 and the outlet 24 of the sampling chamber 22.

In operation, the end cap 3 and base cap 6 are firstly connected to the sample housing 1. The key section 12 is screwed into the cap section 26 of the end cap 3 such that the valve 13 is opened. The sampling apparatus 8 is then lowered into the body of the liquid to be sampled by a supporting cable or wire connected to the key member 12 of the end cap 3. A drive mechanism is provided to provide constant release of the supporting and cable, thereby enabling the sampling apparatus 8 to be lowered through the liquid at a steady rate. As the sampling apparatus 8 is lowered through the liquid, a fluid pressure is applied to the lower surface of the flange section 33 of the collar member 2. This causes the collar member 2 to slide upwardly relative to the inlet aperture 5, thereby exposing the inlet aperture 5. Fluid pressure forces liquid into the aperture 5. As the liquid enters the inner bore of valve section 35 it forces upwards the sealing member 20 to provide a fluid pathway from the aperture 5 to the inner sampling tube 22. The liquid continues to rise within inner sampling tube 22 until it reaches the apex 24. At this point, the liquid overflows from the outlet 24 of the inner sampling tube 22 into the base of the sampling chamber.

Liquid continues to enter the sampling chamber at a constant flow rate as the sampling apparatus 8 descends within the body of liquid, thereby providing a sample which is representative of the entire sampling depth. The constant flow rate is achieved through the arrangement of the sampling apparatus 8 to provide a constant pressure differential between the outlet 24 of the inner sampling tube 22 and the outlet aperture 18 of the end cap 3. As the sampling apparatus 8 descends within the liquid the fluid pressure at inlet aperture 5 increases, as does the pressure at the outlet aperture 18. The pressure at the outlet 24 of the inner sampling tube 22 is less than the pressure at inlet aperture 5 by an amount equivalent to the hydrostatic head provided by the volume of liquid contained within the inner sampling tube 22 and inner bore of the inlet valve 6. Although the pressure at the outlet 24 of the inner sampling tube 22 increases with depth, the difference between this pressure and the pressure at the inlet aperture 5 remains constant irrespective of the depth. As the increase in pressure at the outlet aperture 18 is directly proportional to the increase in pressure at inlet aperture 5 the difference between the pressure at the outlet 24 of the inner sampling tube 22 and the pressure at the outlet aperture 18 also remains constant.

The pressure differential between the outlet 24 of inner sampling tube 22 and the outlet aperture 18 determines the flow rate of liquid into sampling chamber. Therefore, as this differential remains constant, so does the flow rate of liquid into the sampling chamber. As such, sampling flow rate is independent of external fluid pressure, and hence depth, and therefore remains constant along the entire sampling depth. The sampling depth will usually be the entire depth of a body of liquid, although the descent of the sampling apparatus 8 may be controlled to sample a specified depth from the surface to a point within, but not at the bottom of, the depth of the liquid.

Once a sample has been completed, the sampling apparatus 8 is retracted from the liquid. As the sampling apparatus 8 travels upwards within the liquid, fluid pressure acts downwards on the upper surface of the flange member 33 of collar member 2, thereby returning it to the closed position. The weight of the collar member 2 also acts to return it to the closed position. The closed position is defined as any position in which the collar member covers the inlet aperture 5. The collar member also returns to the closed position whenever the sampling apparatus 8 is stationery within the liquid. In this way, the inlet aperture 5 is permanently open during sampling to provide a continuous and constant sample, but is closed as soon as sampling is ceased to prevent further liquid entering the sampling chamber. Once the sampling apparatus 8 is stationery or moving upwardly, the sealing member 20 also returns to the closed position, thereby also preventing release of liquid from the sampling apparatus 8. As the sampling apparatus 8 is raised within liquid, the pressure within the sampling chamber prevents the liquid from entering the chamber via the end cap 3.

Once the sampling apparatus 8 has been retrieved from the liquid, the key member 12 is removed from the cap section 26, thereby closing the valve 13 and preventing the release of liquid or gases from the sampling chamber. Sealing the end cap 3 enables the sampling apparatus to be turned upside down to enable the base cap 6 to be removed from the sample housing 1. The base cap 6 may then be replaced by a sealing cap for storage and transit of the sample.

Once the sample has been taken, it must subsequently be removed from the sampling chamber for analysis. In the simplest scenario, the end cap could be removed and the liquid decanted for analysis. However, for certain sampling techniques, for example Reid Vapour Pressure (RVP) sampling, it is preferable to avoid decanting the liquid as this results in gases such as the light end gases for oil samples, being lost. Additional valve means 39 is provided to enable the removal of the sample from the sampling chamber 1 without decanting.

Once the sampling chamber has been capped, the valve 13 ensures that the sampling chamber is sealed. When it is required to analyse the sample, the sampling valve 39 is screwed into cap section 26, similarly to the key member 12. Sampling valve 39 comprises an internal bore 48 running through the centre of the main valve body 47 and a secondary internal bore 41 connecting with internal bore 48. The central internal bore 48 is narrow at the top of the main body 47 and widens towards the base of the main valve body 47. An end shaft 49 is inserted into the wider section of central internal bore 48, which is threaded at its tip allowing it to be screwed into corresponding threaded section 43 on the internal bore 48. A tightening member 42 is provided at the base of the pin shaft 49. A resilient sealing member 46 is compressed by a spring 45 which acts against a washer 44, and the tightening member 42. A pin 38 extends from pin shaft 49 upwardly within inner bore 48. As tightening member 42 is turned, the pin shaft 49 turns within the threaded section 43 such that the pin 38 is forced upwardly against the sealing member 25 thereby breaking the seal of the valve. In this way a fluid path way is opened from outlet aperture 18 through the central internal bore 48 and additional internal bore 41. A sampling tube 40 is connected to internal bore 41 to transport the sampled liquid from the sampling valve 39 to a suitable analysis apparatus. When a suitable volume of the liquid has been removed from the sampling chamber 1, the tightening member 42 may be turned in the opposite direction thereby retracting the pin 38 and once again sealing the sampling chamber.

Therefore, there is advantageously provided a sampling apparatus which enables a continuous sample to be taken along a specified depth of a liquid, with the sampling flow rate remaining constant along the entire sampling depth, thereby providing a sample which is representative of the liquid along the entire sample depth. An inlet valve is provided which enables liquid to enter the sampling apparatus while the sampling apparatus is moving downwardly within a liquid, and which prevents liquid from entering or exiting the sampling apparatus once the sampling apparatus becomes stationery or moves upwardly. There is also provided means for sealing the chamber once a sample has been taken to permit transit of the sample. Furthermore, there is advantageously provided a sampling valve to enable removing of the sample from the sampling chamber without the need to decant the sample, as is necessary for sampling techniques such as RVP sampling.

It will be appreciated that in further embodiments various modifications to the specific arrangements described above and shown in the drawings may be made. For example, whilst it is described that the main body of the sample housing 1 is preferably cylindrical, it will be appreciated that a housing having a square cross section may also be provided.

The invention claimed is:

1. A liquid sampling apparatus for obtaining a sample from a body of liquid along a depth range, comprising:
   a housing defining a sampling chamber for retaining a sample therein;
   a top aperture of the housing;
   a base aperture of the housing;
   an inlet valve assembly that closes the base aperture of the housing, the inlet valve assembly comprising a body section having an inlet aperture, an inner bore in fluid communication with the inlet aperture, and a collar slidably connected to the body section for opening and closing the inlet aperture of the inlet valve assembly; and
   a sampling tube in fluid communication with the inner bore, having an outlet located within the sampling chamber, at least a portion of the sampling tube extending within the sampling chamber, and defining a fluid pathway between the inlet aperture and the sampling chamber.

2. The apparatus of claim 1, wherein the sampling tube extends a predetermined distance within the sampling chamber.

3. The apparatus of claim 1, wherein the sampling chamber comprises a first end and a second end, and wherein the sampling tube extends into the sampling chamber from the first end and wherein a gap is defined between the second end and the outlet of the sampling tube.

4. The apparatus of claim 1, wherein the inlet valve assembly comprises a non-return valve arranged to permit fluid flow into the sampling chamber.

5. The apparatus of claim 1, wherein the top aperture of the housing is closed by an outlet valve assembly.

6. The apparatus of claim 5, wherein the outlet valve assembly comprises an outlet aperture and a non-return valve.

7. The apparatus of claim 6, further comprising a key member, the key member comprising a key portion; an internal bore; a projection; and a threaded portion for attachment to the outlet valve assembly, wherein threaded attachment of the key member to the outlet valve causes the projection to depress the non-return valve and open a fluid pathway between the sampling chamber and the atmosphere via the internal bore.

8. The apparatus of claim 1, wherein the outlet of the sampling tube extends a first distance from the inlet aperture along a longitudinal axis of the sampling chamber, and an outlet of the sampling chamber is located a second distance from the inlet aperture along the longitudinal axis of the sampling chamber, the second distance being greater than the first distance.

9. The apparatus of claim 1, wherein the sampling tube and inlet aperture are arranged such that in use the outlet of the sampling tube is vertically disposed above the inlet aperture.

10. The apparatus of claim 5, further comprising an end cap and a base cap connected to opposing ends of the housing, the end cap comprising an end cap portion and the outlet valve assembly, and the base cap comprising a base cap portion and the inlet valve assembly.

11. The apparatus of claim 1, wherein the collar is slidable between a first position in which the inlet aperture is covered by the collar, and a second position in which the inlet aperture is exposed by the collar, permitting fluid flow into the inner bore and sampling tube.

12. The apparatus of claim 11, wherein the collar is to the first position.

13. The apparatus of claim 12, further comprising a biasing arrangement to bias the collar to the first position.

14. The apparatus of claim 11, wherein the collar and the body section are arranged such that in use the weight of the collar biases it to the first position.

15. The apparatus of claim 1, wherein the collar comprises a projection extending substantially perpendicular relative to a longitudinal axis of the inlet valve assembly.

* * * * *